(12) United States Patent
Lippa et al.

(10) Patent No.: US 7,098,230 B2
(45) Date of Patent: *Aug. 29, 2006

(54) (−)-1-(3,4-DICHLOROPHENYL)-3-AZABICYCLO[3.1.0]HEXANE, COMPOSITIONS THEREOF, AND USES AS A DOPAMINE-REUPTAKE INHIBITOR

(75) Inventors: Arnold Stan Lippa, Ridgewood, NJ (US); Joseph William Epstein, Monroe, NY (US)

(73) Assignee: DOV Pharmaceutical, Inc., Somerset, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/764,373

(22) Filed: Jan. 23, 2004

(65) Prior Publication Data

US 2004/0157870 A1    Aug. 12, 2004

Related U.S. Application Data

(62) Division of application No. 10/425,545, filed on Apr. 29, 2003, now Pat. No. 6,716,868, which is a division of application No. 09/939,071, filed on Aug. 24, 2001, now Pat. No. 6,569,887.

(51) Int. Cl.
*A61K 31/40*    (2006.01)
(52) U.S. Cl. .................................................. 514/412
(58) Field of Classification Search ................. 514/412
See application file for complete search history.

(56) References Cited

U.S. PATENT DOCUMENTS

| | | | |
|---|---|---|---|
| 3,892,722 A | 7/1975 | Hoffman et al. | |
| 4,022,652 A | 5/1977 | Hirano et al. | |
| 4,088,652 A | 5/1978 | Fanshawe et al. | |
| 4,118,393 A | 10/1978 | Fanshawe et al. | |
| 4,118,417 A | 10/1978 | Epstein | |
| 4,131,611 A | 12/1978 | Fanshawe et al. | |
| 4,196,120 A | 4/1980 | Fanshawe et al. | |
| 4,231,935 A | 11/1980 | Fanshawe et al. | |
| 4,336,268 A | 6/1982 | Bruderer et al. | |
| 4,435,419 A | 3/1984 | Epstein et al. | |
| 4,504,657 A | 3/1985 | Bouzard et al. | |
| 4,521,431 A | 6/1985 | Crookes | |
| 4,591,598 A | 5/1986 | Urbach et al. | |
| 5,039,680 A | 8/1991 | Imperato et al. | |
| 5,075,341 A | 12/1991 | Mendelson et al. | |
| 5,130,430 A | 7/1992 | Shaw | |
| 5,198,459 A | 3/1993 | Imperato et al. | |
| 5,232,934 A | 8/1993 | Downs | |
| 5,488,056 A | 1/1996 | Bodick et al. | |
| 5,556,837 A | 9/1996 | Nestler et al. | |
| 5,556,838 A | 9/1996 | Mayer et al. | |
| 5,574,052 A | 11/1996 | Rose et al. | |
| 5,762,925 A | 6/1998 | Sagen | |
| 5,911,992 A | 6/1999 | Braswell et al. | |
| 5,969,156 A | 10/1999 | Briggs et al. | |
| 5,985,864 A | 11/1999 | Imai et al. | |
| 6,109,269 A | 8/2000 | Rise et al. | |
| 6,121,261 A | 9/2000 | Glatt et al. | |
| 6,194,000 B1 | 2/2001 | Smith et al. | |
| 6,204,284 B1* | 3/2001 | Beer et al. .................. 514/412 |
| 6,245,911 B1 | 6/2001 | Imai et al. | |
| 6,372,919 B1 | 4/2002 | Lippa et al. | |
| 6,569,887 B1 | 5/2003 | Lippa et al. | |
| 6,716,868 B1 | 4/2004 | Lippa et al. | |
| 2004/0102638 A1 | 5/2004 | Russell et al. | |
| 2004/0127541 A1 | 7/2004 | Codd et al. | |
| 2004/0132797 A1 | 7/2004 | Lippa et al. | |
| 2004/0157689 A1 | 8/2004 | Lippa et al. | |
| 2004/0157908 A1 | 8/2004 | Lippa et al. | |

FOREIGN PATENT DOCUMENTS

| | | |
|---|---|---|
| BE | 858683 | 12/1982 |
| BE | 893707 | 12/1982 |

OTHER PUBLICATIONS

Baldessarini, R. *Drugs and The Treatment of Psychiatric Disorders.* Goodman & Gilman's The Pharmacologocal Basis of Therapeutics 9th Edition. Hardman et al. eds. 1996. p. 399 and Ch 18:431-459, McGraw-Hill, New York.

Blum, et al., *Dopamine D2 Receptor Gene Variants; Association and Linkage Studies in Impulsive-Addictive-Compulsive Behavior.* Pharmacogenetics 5:121-141, 1996.

Bray, G, *A Concise Review On The Therapeutics of Obesity.* Nutrition 16:953-960, 2000.

Crown, W. *Economic Outcomes Associated With Tricyclic Antidepressant And Selective Serotonin Reuptate Inhibitor Treatments For Depression:* Acta Psychiatr. Supp. 2000; 403:62-6.

D'Aquila, et al, *The Role Dopoamine In The Mechanism of Action of Antidepressant Drugs.* Eur. J. Pharmacol. 405:365-373, 2000.

(Continued)

*Primary Examiner*—Taofiq Solola
(74) *Attorney, Agent, or Firm*—Jeffrey J. King

(57) ABSTRACT

The present invention relates to (−)-1-(3,4-dichlorophenyl)-3-azabicyclo[3.1.0]hexane and pharmaceutically acceptable salts thereof, compositions comprising (−)-1-(3,4-dichlorophenyl)-3-azabicyclo[3.1.0]hexane or a pharmaceutically acceptable salt thereof, and methods for treating or preventing a disorder alleviated by inhibiting dopamine reuptake. In one embodiment, the disorder is attention-deficit disorder, depression, obesity, Parkinson's disease, a tic disorder, or an addictive disorder. The (−)-1-(3,4-dichlorophenyl)-3-azabicyclo[3.1.0]hexane or pharmaceutically acceptable salt thereof is preferably substantially free of its corresponding (+)-enantiomer.

23 Claims, No Drawings

OTHER PUBLICATIONS

Epstein, et al., *1-Aryl-3-Azabicyclo[3.1.0]Hexanes, A New Series of Non-Narcotic Analgesic Agents*. J. Med. Chem. 24(5):481-90, 1981.

Epstein, et al., *Bicifadine: Non-Narcotic Analgesic Activity of 1-Aryl-3-Azabicyclo[3.1.0]Hexanes*. NIDA Res. Monogr. 41:93-98, 1982.

Frazer, A. *Norepinephrine Involvement In Antidepressant Action*. J. Clin. Psychiatry. 61(10):25-30, 2000.

Fredman, et al., *Partial Response, Nonresponse, and Relapse With Selective Serotonin Reuptake Inhibitors In Major Depression: A Survey of Current "Next-Step" Practices*. J. Clin. Psychiatry 61(6):403-8, 2000.

Hackh's Chemical Dictionary, 4th Edition, 1969, Julius Grant, ed., McGraw-Hill Book Company, New York, pp. 474-475.

Harrison's Principles of Internal Medicine 2485-2503 (Fauci, et al., eds., 14th ed. 1998).

Hitri, et al., *Molecular, Functional and Bilchemical Characteristics of The Dopamine Transporter: Regional Differences and Clinical Relevance*. J. Clin. Pharmacol. 17:1-22, 1994.

Hoffman, et al., *Localization and Dynamic Regulation of Biogenic Amine Transporters In The Mammalian Central Nervous System*. Front. In Neuroendocrinol. 19(3): 187-213, 1998.

Kiyatkin, E. *Dopamine Mechanisms of Cocaine Addition*, Int. J. Neurosci. 78:75-101, 1994.

Kreek, M. *Cocaine, Dopamine and The Endogenous Opiod System*. J. Addict. Dis. 15:73-96, 1996.

Leonhardt, et al., *New Approaches In The Pharmacological Treatment of Obesity*. Eur. J. Nutr. 38:1-13, 1999.

Meyerson, et al., *Allosteric Interation Between The Site Labeled by [3H]imipramine and The Serotonin Transporter In Human Platelets*. J. Neurochem. 48(2):560-65, 1987.

Nagatsu, et al., *Changes In Cytokines And Neorotrophins In Parkinson's Disease*. J. Neural. Transm. Suppl. 60:277-290, 2000.

Noble, E., *Polymorphisms of The D2 Dopamine Receptor Gene and Alcoholism and Other Substance Use Disorders*. Alcohol. Supp. 2:35-43, 1994.

Porter, et al., *Single Dose Comparison of Bicifadine, Codeine, and Placebo in Postoperative Pain*. Current Therapeutic Research. 30(3):156-160, Aug. 1981.

Scates, et al., *Reboxetine: A Selective Norepinephrine Reuptate Inhibitor For The Treatment Of Depression*. Ann. Pharmacother. 34(11):1302-12, 2000.

Simon, et al., *TCAs or SSRIs As Initial Therapy For Depression?* J. of Family Practice. 48:845-46, 1999.

Stacy, et al., *Treatment Options for Early Parkinson's Disease*. Am. Fam. Phys. 53:1281-87, 1996.

Sullivan, et al., *Mechanisms of Appetite Modulation By Drugs*, Federation Proceedings, vol. 44, No. 1, Part 1, pp. 139-144, 1985.

Wang, et al., *The Oral Analgesic Efficacy of Bicifadine Hydrochloride In Postoperative Pain*. J. Clin. Pharmacol. 22(4):160-164, Apr. 1982.

Wong, et al., *Reboxetine: A PharmacologicallyPotent, Selective, and Specific Norepinephrine Reuptake Inhibitor*. Biol. Psychiatry. 47(9):818-29, 2000.

\* cited by examiner

(-)-1-(3,4-DICHLOROPHENYL)-3-AZABICYCLO[3.1.0]HEXANE, COMPOSITIONS THEREOF, AND USES AS A DOPAMINE-REUPTAKE INHIBITOR

This application is a divisional of application Ser. No. 10/425,545, filed on Apr. 29, 2003, now U.S. Pat. No. 6,716,868 which is a divisional of application Ser. No. 09/939,071, filed on Aug. 24, 2001, now U.S. Pat. No. 6,569,887, dated May 27, 2003.

1. FIELD OF THE INVENTION

The present invention relates to (−)-1-(3,4-dichlorophenyl)-3-azabicyclo[3.1.0]hexane and pharmaceutically acceptable salts thereof, compositions comprising (−)-1-(3,4-dichlorophenyl)-3-azabicyclo[3.1.0]hexane or a pharmaceutically acceptable salt thereof and methods for treating or preventing a disorder alleviated by inhibiting dopamine reuptake comprising administering to a patient (−)-1-(3,4-dichlorophenyl)-3-azabicyclo[3.1.0]hexane or a pharmaceutically acceptable salt thereof.

2. BACKGROUND OF THE INVENTION

Dopamine is a monoamine neurotransmitter that plays a critical role in the function of the hypothalamic-pituitary-adrenal axis and in the integration of information in sensory, limbic, and motor systems. The primary mechanism for termination of dopamine neurotransmission is through reuptake of released dopamine by $Na^+/Cl^-$-dependent plasma membrane transporters (Hoffman et al., 1998, *Front. Neuroendocrinol.* 19(3):187–231). Depending on the surrounding ionic conditions, the dopamine transporter can function as a mediator of both inward directed dopamine transport (i.e., "reuptake") and outward directed dopamine transport (i.e., "release"). The functional significance of the dopamine transporter is its regulation of dopamine neurotransmission by terminating the action of dopamine in a synapse via reuptake (Hitri et al., 1994, *Clin. Pharmacol.* 17:1–22).

Attention deficit disorder is a learning disorder involving developmentally inappropriate inattention with or without hyperactivity. The primary signs of attention deficit disorder are a patient's inattention and impulsivity. Inappropriate inattention causes increased rates of activity or reluctance to participate or respond. A patient suffering from attention deficit disorder exhibits a consistent pattern of inattention and/or hyperactivity-impulsivity that is more frequent and severe than is typically observed in individuals at a comparable level of development. (See, e.g., U.S. Pat. No. 6,121,261 to Glatt et al.).

Patients having Parkinson's disease display jittery movements of the limbs, head, and jaw. Parkinson's disease is associated with bradykinesia, rigidity and falling (Stacy et al., 1996, *Am. Fam. Phys.* 53:1281–1287). The movement disturbances observed in Parkinson's disease patients result from degeneration of dopamine neurons, loss of nerve terminals, and dopamine deficiency. It is hypothesized that the cause of the degeneration of the dopamine neurons results from apoptosis resulting from increased levels of cytokines (Nagatsu et al., 2000, *J. Neural Transm. Suppl.* 60:277–290). Abnormalities in the dopamine transporter have been implicated in Parkinson's disease (Hitri et al., 1994, *Clin. Neuropharmacol.* 17:1–22). Symptoms of Parkinson's disease can be attenuated by compounds like pergolide which mimics the actions of dopamine or by compounds that inhibit dopamine metabolism (e.g., carbidopa) or by dopamine precursors (e.g., L-DOPA±carbidopa).

Appetite suppression is a reduction, a decrease or, in cases of excessive food consumption, an amelioration in appetite. This suppression reduces the desire or craving for food. Appetite suppression can result in weight loss or weight control as desired. Appetite suppression can regulate food intake through drug administration directed to one or more systems known to play a role in food digestion. See, for example, Sullivan et al., "Mechanisms of Appetite Modulation By Drugs," Federation Proceedings, Volume 44, No. 1, Part 1, pages 139–144 (1985). Methods for controlling appetite suppression include the regulation of serotonin level, thermogenesis and the inhibition of lipogenesis. (See e.g., U.S. Pat. No. 5,911,992 to Braswell et al.).

Depression is one of the most common of the mental illnesses, having a morbidity rate of over 10% in the general population. Depression is characterized by feelings of intense sadness, despair, mental slowing, loss of concentration, pessimistic worry, agitation, and self-deprecation (*Harrison's Principles of Internal Medicine* 2490–2497 (Fauci et al. eds., $14^{th}$ ed. 1998)). Depression can have physical manifestations including insomnia, hypersomnia, anorexia, weight loss, overeating, decreased energy, decreased libido, and disruption of normal circadian rhythms of activity, body temperature, and endosine functions. In fact, as many as 10% to 15% of depressed individuals display suicidal behavior. R. J. Baldessarini, *Drugs and the Treatment of Psychiatric Disorders: Depression and Mania*, in Goodman and Gilman's The Pharmacological Basis of Therapeutics 431 ($9^{th}$ ed. 1996). Anhedonia is one of the principal (core) symptoms of depression. Dopamine pathways have been linked to pleasure seeking behaviors, and strategies to increase synaptic concentrations of dopamine have been proposed as antidepressant therapies. (See e.g., D'Aquila et al., 2000, *Eur. J. Pharmacol.* 405:365–373).

Obesity is commonly referred to as a condition of increased body weight due to excessive fat. Drugs to treat obesity can be divided into three groups: (1) those that decrease food intake, such as drugs that interfere with monoamine receptors, such as noradrenergic receptors, serotonin receptors, dopamine receptors, and histamine receptors; (2) those that increase metabolism; and (3) those that increase thermogenesis or decrease fat absorption by inhibiting pancreatic lipase (Bray, 2000, *Nutrition* 16:953–960 and Leonhardt et al., 1999, *Eur. J. Nutr.* 38:1–13).

Many drugs can cause physical and/or psychological addiction. Those most well known drugs include opiates, such as heroin, opium and morphine; sympathomimetics, including cocaine and amphetamines; sedative-hypnotics, including alcohol, benzodiazepines and barbiturates; and nicotine, which has effects similar to opioids and sympathomimetics. Drug addiction is characterized by a craving or compulsion for taking the drug and an inability to limit its intake. Additionally, drug dependence is associated with drug tolerance, the loss of effect of the drug following repeated administration, and withdrawal, the appearance of physical and behavioral symptoms when the drug is not consumed. Sensitization occurs if repeated administration of a drug leads to an increased response to each dose. Tolerance, sensitization, and withdrawal are phenomena evidencing a change in the central nervous system resulting from continued use of the drug. This change motivates the addicted individual to continue consuming the drug despite serious social, legal, physical and/or professional consequences. (See, e.g., U.S. Pat. No. 6,109,269 to Rise et al.).

Cocaine addiction remains one of the major health problems in the United States. Fundamental studies from many laboratories have shown that cocaine blocks the uptake of dopamine from the synaptic cleft of the dopamine transporter (Kreek, 1996, *J. Addict. Dis.* 15:73–96). For example, the inhibition action of cocaine on reuptake of released dopamine, however, does not fully explain the development and maintenance of addictive behavior. Coexistence of functionally antagonistic, inhibition actions of cocaine on the dopamine release and reuptake of the released dopamine might be responsible for fluctuations in dopamine transmission (Kiyatkin, 1994, *Int. J. Neurosci.* 78:75–101).

Certain pharmaceutical agents have been administered for treating addiction. U.S. Pat. No. 5,556,838 to Mayer et al. discloses the use of nontoxic NMDA-blocking agents co-administered with an addictive substance to prevent the development of tolerance or withdrawal symptoms. U.S. Pat. No. 5,574,052 to Rose et al. discloses co-administration of an addictive substance with an antagonist to partially block the pharmacological effects of the substance. U.S. Pat. No. 5,075,341 to Mendelson et al. discloses the use of a mixed opiate agonist/antagonist to treat cocaine and opiate addiction. U.S. Pat. No. 5,232,934 to Downs discloses administration of 3-phenoxypyridine to treat addiction. U.S. Pat. Nos. 5,039,680 and 5,198,459 to Imperato et al. disclose using a serotonin antagonist to treat chemical addiction. U.S. Pat. No. 5,556,837 to Nestler et. al. discloses infusing BDNF or NT-4 growth factors to inhibit or reverse neurological adaptive changes that correlate with behavioral changes in an addicted individual. U.S. Pat. No. 5,762,925 to Sagan discloses implanting encapsulated adrenal medullary cells into a patient's central nervous system to inhibit the development of opioid intolerance. Bupropion has dopamine reuptake inhibition properties and is used to treat nicotine addiction.

Dopaminergic reward pathways have been implicated in disorders resulting from addictive behaviors. Variants of the dopamine D2 receptor gene have been associated with alcoholism, obesity, pathological gambling, attention deficit hyperactivity disorder, Tourette syndrome, cocaine dependence, nicotine dependence, polysubstance abuse, and other drug dependency (Noble, 1994, *Alcohol Supp.* 2:35–43 and Blum et al., 1995, *Pharmacogenetics* 5:121–141). Since reduced dopaminergic functions have been found in individuals with a minor A1 allele of the dopamine D2 receptor, it has been suggested that the dopamine D2 receptor may be a reinforcement or reward gene (Noble, 1994, *Alcohol Supp.* 2:35–43). Furthermore, several studies suggest that an associate of dopamine D2 receptor gene polymorphisms are associated with impulsive-addictive-compulsive behavior, i.e., "Reward Deficiency Syndrome" (reviewed by Blum et al., 1995, *Pharmacogenetics* 5:121–141).

U.S. Pat. No. 4,435,419 to Epstein et al. discloses racemic, (±)-1-(3,4-dichlorophenyl)-3-azabicyclo[3.1.0]hexane for use as an anti-depressant agent.

U.S. Pat. No. 6,204,284 to Beer et al. discloses racemic, (±)-1-(3,4-dichlorophenyl)-3-azabicyclo[3.1.0]hexane for use in the prevention or relief of a withdrawal syndrome resulting from addition to drugs and for the treatment of chemical dependencies.

Administration of a racemic, i.e., 50:50, mixture of the (+)- and the (−)-enantiomer of any drug, for example (±)-1-(3,4-dichlorophenyl)-3-azabicyclo[3.1.0]hexane, to a patient can be disadvantageous. First, the racemic mixture might be less pharmacologically active than one of its enantiomers, rendering racemic drugs inherently inefficient. Second, the racemic mixture may be more toxic to a patient than one of its enantiomers, so that administration of a racemic mixture can lead to undesirable side effects in a patient.

Accordingly, there is a clear need in the art for an enantiomer, the enantiomer being preferably substantially free of the corresponding opposite enantiomer, which would overcome one or both of the aforementioned disadvantages.

Citation of identification of any reference in Section 2 of this application is not to be construed as an admission that such reference is prior art to the present application.

3. SUMMARY OF THE INVENTION

In one embodiment, the invention provides (−)-1-(3,4-dichlorophenyl)-3-azabicyclo[3.1.0]hexane and pharmaceutically acceptable salts thereof. (−)-1-(3,4-dichlorophenyl)-3-azabicyclo[3.1.0]hexane and pharmaceutically acceptable salts thereof are useful for treating or preventing a disorder alleviated by inhibiting dopamine reuptake.

The present invention further provides compositions comprising an effective amount of (−)-1-(3,4-dichlorophenyl)-3-azabicyclo[3.1.0]hexane or a pharmaceutically acceptable salt thereof. The present compositions can additionally comprise a pharmaceutically acceptable vehicle. These compositions are useful for treating or preventing a disorder alleviated by inhibiting dopamine reuptake.

In another embodiment, the invention provides a method for treating or preventing a disorder alleviated by inhibiting dopamine reuptake, comprising administering to a patient in need of such treatment or prevention an effective amount of (−)-1-(3,4-dichlorophenyl)-3-azabicyclo[3.1.0]hexane or a pharmaceutically acceptable salt thereof.

In still another embodiment, the invention provides a method for treating or preventing attention-deficit disorder, depression, obesity, Parkinson's disease, a tic disorder, or an addictive disorder, comprising administering to a patient in need of such treatment or prevention an effective amount of (−)-1-(3,4-dichlorophenyl)-3-azabicyclo[3.1.0]hexane or a pharmaceutically acceptable salt thereof.

Preferably, (−)-1-(3,4-dichlorophenyl)-3-azabicyclo[3.1.0]hexane or a pharmaceutically acceptable salt thereof, particularly when used in the present methods or compositions, is substantially free of its corresponding (+)-enantiomer. In a preferred embodiment, (−)-1-(3,4-dichlorophenyl)-3-azabicyclo[3.1.0]hexane or a pharmaceutically acceptable salt thereof substantially free of its corresponding (+)-enantiomer is used to treat or prevent a disorder alleviated by selectively inhibiting dopamine uptake. Use according to this preferred embodiment, surprisingly and advantageously does not block norepinephrine or serotonin transport, in particular, norepinephrine or serotonin uptake. It has unexpectedly been discovered that use of (−)-1-(3,4-dichlorophenyl)-3-azabicyclo[3.1.0]hexane or a pharmaceutically acceptable salt thereof substantially free of its corresponding (+) enantiomer to treat or prevent a disorder alleviated by inhibiting dopamine uptake avoids side effects such as cardiovascular effects, sleep interruption, hypertension or sexual dysfunction associated with norepinephrine or serotonin uptake inhibitors.

In still another embodiment, the invention provides a method for obtaining (−)-1-(3,4-dichlorophenyl)-3-azabicyclo[3.1.0]hexane substantially free of its corresponding (+)-enantiomer, comprising the steps of:

(a) passing a solution of an organic eluent and (±)-1-(3,4-dichlorophenyl)-3-azabicyclo[3.1.0]hexane over a chiral polysaccharide stationary phase to provide a first fraction containing (−)-1-(3,4-dichlorophenyl)-3-azabicyclo[3.1.0] hexane; and (b) passing the first fraction over the chiral polysaccharide stationary phase to provide a second fraction containing (−)-1-(3,4-dichlorophenyl)-3-azabicyclo[3.1.0]hexane substantially free of its corresponding (+)-enantiomer.

In still another embodiment, the invention provides a method for obtaining (−)-1-(3,4-dichlorophenyl)-3-azabicyclo[3.1.0]hexane substantially free of its corresponding (+)-enantiomer, comprising the steps of:

(a) passing a solution of an organic eluent and (+)-1-(3,4-dichlorophenyl)-3-azabicyclo[3.1.0]hexane over a chiral polysaccharide stationary phase to provide a first fraction containing (−)-1-(3,4-dichlorophenyl)-3-azabicyclo[3.1.0] hexane;

(b) concentrating the first fraction to provide a residue; and (c) passing a solution of an organic eluent and the residue over a chiral polysaccharide stationary phase to provide a second fraction containing (−)-1-(3,4-dichlorophenyl)-3-azabicyclo[3.1.0]hexane substantially free of its corresponding (+)-enantiomer.

The present invention may be understood more fully by reference to the detailed description and examples, which are intended to exemplify non-limiting embodiments of the invention.

4. DETAILED DESCRIPTION OF THE INVENTION 4.1 Definitions

The term "substantially free of its corresponding (+)-enantiomer" means containing no more than about 5% w/w of the corresponding (+)-enantiomer, preferably no more than about 2% w/w of the corresponding (+)-enantiomer, more preferably no more than about 1% w/w of the corresponding (+)-enantiomer.

The term "corresponding (+)-enantiomer" when used in connection with (−)-1-(3,4-dichlorophenyl)-3-azabicyclo [3.1.0]hexane or a pharmaceutically acceptable salt thereof means "(+)-1-(3,4-dichlorophenyl)-3-azabicyclo[3.1.0]hexane" or a pharmaceutically acceptable salt thereof.

A "patient" is an animal, including, but not limited to, an animal such a cow, monkey, horse, sheep, pig, chicken, turkey, quail, cat, dog, mouse, rat, rabbit, and guinea pig, and is more preferably a mammal, and most preferably a human.

The phrase "pharmaceutically acceptable salt" as used herein is a salt formed from an acid and the basic nitrogen group of (−)-1-(3,4-dichlorophenyl)-3-azabicyclo[3.1.0] hexane. Preferred salts include, but are not limited, to sulfate, citrate, acetate, oxalate, chloride, bromide, iodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

4.2 (−)-1-(3,4-Dichlorophenyl)-3-Azabicyclo[3.1.0]Hexane (−)-1-(3,4-dichlorophenyl)-3-azabicyclo[3.1.0]hexane, preferably that substantially free of its corresponding (+)-enantiomer, can be obtained from (+)-1-(3,4-dichlorophenyl)-3-azabicyclo[3.1.0]hexane using chiral chromatographic methods, such as high-performance liquid chromatography ("HPLC") with a suitable, preferably chiral, column. (±)-1-(3,4-dichlorophenyl)-3-azabicyclo [3.1.0]hexane is obtainable using methods disclosed in U.S. Pat. No. 4,435,419 to Epstein et al.

In a preferred embodiment, (−)-1-(3,4-dichlorophenyl)-3-azabicyclo[3.1.0]hexane is obtained by passing a solution of an organic eluent and (±)-1-(3,4-dichlorophenyl)-3-azabicyclo[3.1.0]hexane over a chiral polysaccharide stationary phase. Preferably, the polysaccharide is starch or a starch derivative. Advantageously, the chiral stationary phase is within a chiral HPLC column, for example, a CHIRALPAK AD column manufactured by Daicel and commercially available from Chiral Technologies, Inc., Exton, Pa., more preferably a 1 cm×25 cm CHIRALPAK AD HPLC column. The preferred eluent is a hydrocarbon solvent adjusted in polarity with a miscible polar organic solvent. Preferably, the organic eluent contains a non-polar, hydrocarbon solvent present in about 95% to about 99.5% (volume/volume) and a polar organic solvent present in about 5 to about 0.5% (volume/volume). In a preferred embodiment, the hydrocarbon solvent is hexane and the miscible polar organic solvent is isopropylamine.

Passing the solution of the organic eluent and (±)-1-(3,4-dichlorophenyl)-3-azabicyclo[3.1.0]hexane over the chiral polysaccharide stationary phase provides a first fraction (i.e., one or more fractions) containing (−)-1-(3,4-dichlorophenyl)-3-azabicyclo[3.1.0]hexane. The first fraction can be directly passed over the chiral polysaccharide stationary phase to provide a second fraction (i.e., one or more fractions) containing (−)-1-(3,4-dichlorophenyl)-3-azabicyclo [3.1.0]hexane substantially free of its corresponding (+)-enantiomer. Alternatively, the first fraction can be concentrated to provide a residue that can be diluted with an organic eluent, and the resulting solution can be passed over the chiral polysaccharide stationary phase to provide a second fraction containing (−)-1-(3,4-dichlorophenyl)-3-azabicyclo[3.1.0]hexane substantially free of its corresponding (+)-enantiomer. Either way, the second fraction(s) can be concentrated, preferably in vacuo, to obtain a solid form of (−)-1-(3,4-dichlorophenyl)-3-azabicyclo[3.1.0]hexane substantially free of its corresponding (+)-enantiomer.

4.3 Therapeutic Uses of (−)-1-(3,4-Dichlorophenyl)-3-Azabicyclo[3.1.0]Hexane

In accordance with the invention, (−)-1-(3,4-dichlorophenyl)-3-azabicyclo[3.1.0]hexane or a pharmaceutically acceptable salt thereof is administered to a patient, preferably a mammal, more preferably a human, for the treatment or prevention of a disorder alleviated by inhibiting dopamine reuptake. In one embodiment, "treatment" or "treating" refers to an amelioration of a disorder alleviated by inhibiting dopamine reuptake, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disorder alleviated by inhibiting dopamine reuptake, either physically, e.g., normalization of a discernible symptom, physiologically, e.g., normalization of a physical parameter, or both. In yet another embodiment, "treatment" or "treating" refers to delaying the onset of a disorder alleviated by inhibiting dopamine reuptake.

In certain embodiments, (−)-1-(3,4-dichlorophenyl)-3-azabicyclo[3.1.0]hexane or a pharmaceutically acceptable salt thereof is administered to a patient, preferably a mammal, more preferably a human, as a preventative measure against acquiring a disorder alleviated by inhibiting dopamine reuptake. As used herein, "prevention" or "preventing" refers to a reduction of the risk of acquiring a disorder alleviated by inhibiting dopamine reuptake or to the reduction of the risk of recurrence of the disorder once cured or restored to a normal state. In one embodiment, (−)-1-(3,4-dichlorophenyl)-3-azabicyclo[3.1.0]hexane or a pharmaceutically acceptable salt thereof is administered as a preventative measure to a patient. According to this embodiment, the patient can have a genetic predisposition to a disorder alleviated by inhibiting dopamine reuptake, such as a family history of biochemical imbalance in the brain, or a non-genetic predisposition to a disorder alleviated by inhibiting dopamine reuptake. Accordingly, the (−) 1-(3,4-dichlorophenyl)-3-azabicyclo[3.1.0]hexane and pharmaceutically acceptable salts thereof can be used for the treatment of one manifestation of a disorder alleviated by inhibiting dopamine reuptake and prevention of another.

4.3.1 Disorders Alleviated Using (−)-1-(3,4-Dichlorophenyl)-3-Azabicyclo[3.1.0]Hexane (−)-1-(3,4-dichlorophenyl)-3-azabicyclo[3.1.0]hexane and pharmaceutically acceptable salts thereof are useful for treating or preventing endogenous disorders alleviated by inhibiting dopamine reuptake. Such disorders include, but are not limited to, attention-deficit disorder, depression, obesity, Parkinson's disease, tic disorders, and addictive disorders.

Disorders alleviated by inhibiting dopamine reuptake are not limited to the specific disorders described herein, as many types of disorders may manifest from the primary disorder. For example, as disclosed in U.S. Pat. No. 6,132,724 to Blum, attention deficit hyperactivity disorder may manifest itself in the form of alcohol abuse, drug abuse, obsessive compulsive behaviors, learning disorders, reading problems, gambling, manic symptoms, phobias, panic attacks, oppositional defiant behavior, conduct disorder, academic problems in school, smoking, abnormal sexual behaviors, schizoid behaviors, somatization, depression, sleep disorders, general anxiety, stuttering, and tics disorders. All these behaviors and others described herein as associated with disorders alleviated by inhibiting dopamine reuptake are included as disorders as part of this invention. Additionally, clinical terms used herein for many specific disorders are found in the Quick Reference to the Diagnostic Criteria From DSM-IV (Diagnostic and Statistical Manual of Mental Disorders, Fourth Edition), The American Psychiatric Association, Washington, D.C., 1994, 358 pages. Specific disorders whose definitions can be found in this reference are described below.

Attention-deficit disorders include, but are not limited to, Attention-Deficit/Hyperactivity Disorder, Predominately Inattentive Type; Attention-Deficit/Hyperactivity Disorder, Predominately Hyperactivity-Impulsive Type; Attention-Deficit/Hyperactivity Disorder, Combined Type; Attention-Deficit/Hyperactivity Disorder not otherwise specified (NOS); Conduct Disorder; Oppositional Defiant Disorder; and Disruptive Behavior Disorder not otherwise specified (NOS).

Depressive disorders include, but are not limited to, Major Depressive Disorder, Recurrent; Dysthymic Disorder; Depressive Disorder not otherwise specified (NOS); and Major Depressive Disorder, Single Episode.

Parkinson's disease includes, but is not limited to, neuroleptic-induced parkinsonism.

Addictive disorders include, but are not limited to, eating disorders, impulse control disorders, alcohol-related disorders, nicotine-related disorders, amphetamine-related disorders, cannabis-related disorders, cocaine-related disorders, hallucinogen use disorders, inhalant-related disorders, and opioid-related disorders, all of which are further sub-classified as listed below.

Eating disorders include, but are not limited to, Bulimia Nervosa, Nonpurging Type; Bulimia Nervosa, Purging Type; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder, with delusions; Alcohol Abuse; Alcohol Intoxication; Alcohol Withdrawal; Alcohol Intoxication Delirium; Alcohol Withdrawal Delirium; Alcohol-Induced Persisting Dementia; Alcohol-Induced Persisting Amnestic Disorder; Alcohol Dependence; Alcohol-Induced Psychotic Disorder, with hallucinations; Alcohol-Induced Mood Disorder; Alcohol-Induced Anxiety Disorder; Alcohol-Induced Sexual Dysfunction; Alcohol-Induced Sleep Disorder; Alcohol-Related Disorder not otherwise specified (NOS); Alcohol Intoxication; and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

Cannabis-related disorders include, but are not limited to, Cannabis Dependence; Cannabis Abuse; Cannabis Intoxication; Cannabis Intoxication Delirium; Cannabis-Induced Psychotic Disorder, with delusions; Cannabis-Induced Psychotic Disorder with hallucinations; Cannabis-Induced Anxiety Disorder; Cannabis Related Disorder not otherwise specified (NOS); and Cannabis Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-use disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence; Inhalant Abuse; Inhalant Intoxication; Inhalant Intoxication Delirium; Inhalant-Induced Psychotic Disorder, with delusions; Inhalant-Induced Psychotic Disorder with hallucinations; Inhalant-Induced Anxiety Disorder; Inhalant Related Disorder not otherwise specified (NOS); and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder, with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

Tic disorders include, but are not limited to, Tourette's Disorder, Chronic Motor or Vocal Tic Disorder, Transient Tic Disorder, Tic Disorder not otherwise specified (NOS), Stuttering, Autistic Disorder, and Somatization Disorder.

4.4 Therapeutic/Prophylactic Administration and Composition of the Invention

Due to their activity, (−)-1-(3,4-dichlorophenyl)-3-azabicyclo[3.1.0]hexane and pharmaceutically acceptable salts thereof are advantageously useful in veterinary and human medicine. As described above, (−)-1-(3,4-dichlorophenyl)-3-azabicyclo[3.1.0]hexane and pharmaceutically acceptable salts thereof are useful for the treatment or prevention of a disorder alleviated by inhibiting dopamine reuptake.

When administered to a patient, (−)-1-(3,4-dichlorophenyl)-3-azabicyclo[3.1.0]hexane or a pharmaceutically acceptable salt thereof is preferably administered as component of a composition that optionally comprises a pharmaceutically acceptable vehicle. The present compositions, which comprise an effective amount of (−)-1-(3,4-dichlorophenyl)-3-azabicyclo[3.1.0]hexane or a pharmaceutically acceptable salt thereof, are preferably administered orally. The compositions of the invention can also be administered by any other convenient route, for example, by infusion or bolus injection, by absorption through epithelial or mucocutaneous linings (e.g., oral mucosa, rectal, and intestinal mucosa, etc.) and can be administered together with another biologically active agent. Administration can be systemic or local. Various delivery systems are known, e.g., encapsulation in liposomes, microparticles, microcapsules, and capsules, and can be used to administer (−)-1-(3,4-dichlorophenyl)-3-azabicyclo[3.1.0]hexane and pharmaceutically acceptable salts thereof.

In certain embodiments, the present compositions can comprise (−)-1-(3,4-dichlorophenyl)-3-azabicyclo[3.1.0] hexane and/or one or more pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of (−)-1-(3,4-dichlorophenyl)-3-azabicyclo[3.1.0]hexane or a pharmaceutically acceptable salt thereof into the bloodstream.

In specific embodiments, it may be desirable to administer (−)-1-(3,4-dichlorophenyl)-3-azabicyclo[3.1.0]hexane or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce (−)-1-(3,4-dichlorophenyl)-3-azabicyclo[3.1.0]hexane or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, (−)-1-(3,4-dichlorophenyl)-3-azabicyclo[3.1.0]hexane and pharmaceutically acceptable salts thereof can be formulated as a suppository, with traditional binders and vehicles such as triglycerides.

In another embodiment, (−)-1-(3,4-dichlorophenyl)-3-azabicyclo[3.1.0]hexane and pharmaceutically acceptable salts thereof can be delivered in a vesicle, in particular a liposome (see Langer, 1990, *Science* 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, (−)-1-(3,4-dichlorophenyl)-3-azabicyclo[3.1.0]hexane and pharmaceutically acceptable salts thereof can be delivered in a controlled-release system (see, e.g., Goodson, in Medical Applications of Controlled Release, supra, vol. 2, pp. 115–138 (1984)). Other controlled-release systems discussed in the review by Langer, 1990, *Science* 249:1527–1533) may be used. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of a target of (−)-1-(3,4-dichlorophenyl)-3-azabicyclo[3.1.0] hexane or a pharmaceutically acceptable salt thereof, e.g., the spinal column or brain, thus requiring only a fraction of the systemic dose.

The present compositions can optionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile.

Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in *Remington's Pharmaceutical Sciences*, Alfonso R. Gennaro ed., Mack Publishing Co. Easton, Pa., 19th ed., 1995, pp. 1447 to 1676, incorporated herein by reference.

In a preferred embodiment, (−)-1-(3,4-dichlorophenyl)-3-azabicyclo[3.1.0]hexane or a pharmaceutically acceptable salt thereof is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharin, cellulose and magnesium carbonate. Such vehicles are preferably of pharmaceutical grade. Typically, compositions for intravenous administration comprise sterile isotonic aqueous buffer. Where necessary, the compositions may also include a solubilizing agent.

In another embodiment, (−)-1-(3,4-dichlorophenyl)-3-azabicyclo[3.1.0]hexane or a pharmaceutically acceptable salt thereof can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where (−)-1-(3,4-dichlorophenyl)-3-azabicyclo[3.1.0]hexane or a pharmaceutically acceptable salt thereof is to be administered by infusion, it can be dispensed, for example, with an infusion bottle containing sterile pharmaceutical grade water or saline. Where the (−)-1-(3,4-dichlorophenyl)-3-azabicyclo[3.1.0]hexane or a pharmaceutically acceptable salt thereof is administered by injection, an ampoule of sterile water for injection or saline can be provided so that the ingredients may be mixed prior to administration.

The amount of (−)-1-(3,4-dichlorophenyl)-3-azabicyclo[3.1.0]hexane or a pharmaceutically acceptable salt thereof that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed will also depend on the route of administration, and the seriousness of the disease or disorder, and should be decided according to the judgment of the practitioner and each patient's circumstances. However, suitable dosage ranges for oral administration are generally about 0.001 milligram to about 200 milligrams of (−)-1-(3,4-dichlorophenyl)-3-azabicyclo[3.1.0]hexane or a pharmaceutically acceptable salt thereof per kilogram body weight per day. In specific embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to about 50 milligrams per kilogram body weight per day, and yet more preferably about 1 milligram to about 30 milligrams per kilogram body weight per day. In another embodiment, the oral dose is about 1 milligram to about 3 milligrams of (−)-1-(3,4-dichlorophenyl)-3-azabicyclo[3.1.0]hexane or a pharmaceutically acceptable salt thereof per kilogram body weight per day. In another embodiment, the oral dose is about 0.1 milligram to about 2 milligrams of (−)-1-(3,4-dichlorophenyl)-3-azabicyclo[3.1.0]hexane or a pharmaceutically acceptable salt thereof per kilogram body weight one to two times per day. The dosage amounts described herein refer to total amounts administered; that is, if (−)-1-(3,4-dichlorophenyl)-3-azabicyclo[3.1.0]hexane and/or one or more pharmaceutically acceptable salts thereof are administered, the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of (−)-1-(3,4-dichlorophenyl)-3-azabicyclo[3.1.0]hexane or a pharmaceutically acceptable salt thereof per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The invention also provides pharmaceutical packs or kits comprising one or more vessels containing (−)-1-(3,4-dichlorophenyl)-3-azabicyclo[3.1.0]hexane or a pharmaceutically acceptable salt thereof. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains (−)-1-(3,4-dichlorophenyl)-3-azabicyclo[3.1.0] hexane and/or one or more pharmaceutically acceptable salts thereof. In another embodiment, the kit comprises a therapeutic agent and (−)-1-(3,4-dichlorophenyl)-3-azabicyclo [3.1.0]hexane or a pharmaceutically acceptable salt thereof.

(−)-1-(3,4-dichlorophenyl)-3-azabicyclo[3.1.0]hexane and pharmaceutically acceptable salts thereof are preferably assayed in vitro or in vivo, for the desired therapeutic or prophylactic activity, prior to use in humans. For example, in vitro assays can be used to determine whether it is preferable to administer (−)-1-(3,4-dichlorophenyl)-3-azabicyclo[3.1.0]hexane, a pharmaceutically acceptable salt thereof, and/or another therapeutic agent. Animal model systems can be used to demonstrate safety and efficacy.

Other methods will be known to the skilled artisan and are within the scope of the invention.

4.5 Combination Therapy

In certain embodiments of the present invention, (−)-1-(3,4-dichlorophenyl)-3-azabicyclo[3.1.0]hexane or a pharmaceutically acceptable salt thereof can be used in combination therapy with at least one other therapeutic agent. (−)-1-(3,4-dichlorophenyl)-3-azabicyclo[3.1.0]hexane or a pharmaceutically acceptable salt thereof and the other therapeutic agent can act additively or, more preferably, synergistically. In a preferred embodiment, (−)-1-(3,4-dichlorophenyl)-3-azabicyclo[3.1.0]hexane or a pharmaceutically acceptable salt thereof is administered concurrently with the administration of another therapeutic agent, which can be part of the same composition as or in a different composition from that comprising (−)-1-(3,4-dichlorophenyl)-3-azabicyclo[3.1.0]hexane or a pharmaceutically acceptable salt thereof. The other therapeutic agent can be useful for treating and/or preventing (as defined herein) a secondary malady resulting from a disorder alleviated by inhibiting dopamine reuptake. In another embodiment, (−)-1-(3,4-dichlorophenyl)-3-azabicyclo[3.1.0]hexane or a pharmaceutically acceptable salt thereof is administered prior or subsequent to administration of another therapeutic agent. As many of the disorders for which (−)-1-(3,4-dichlorophenyl)-3-azabicyclo[3.1.0]hexane and pharmaceutically acceptable salts thereof are useful in treating are chronic, in one embodiment combination therapy involves alternating between administering a composition comprising a (−)-1-(3,4-dichlorophenyl)-3-azabicyclo[3.1.0]hexane or a pharmaceutically acceptable salt thereof and a composition comprising another therapeutic agent. The duration of administration of (−)-1-(3,4-dichlorophenyl)-3-azabicyclo [3.1.0]hexane, a pharmaceutically acceptable salt thereof, or the other therapeutic agent can be, e.g., one month, three months, six months, a year, or for more extended periods, such as the patient's lifetime. In certain embodiments, when (−)-1-(3,4-dichlorophenyl)-3-azabicyclo[3.1.0]hexane or a pharmaceutically acceptable salt thereof is administered concurrently with another therapeutic agent that potentially produces adverse side effects including, but not limited to, toxicity, the other therapeutic agent can advantageously be administered at a dose that falls below the threshold at which the adverse side effect is elicited.

The other therapeutic agent can be an anti-attention-deficit-disorder agent. Useful anti-attention-deficit-disorder agents include, but are not limited to, methylphenidate; dextroamphetamine; tricyclic antidepressants, such as imipramine, desipramine, and nortriptyline; and a psychostimulant, such as pemoline and deanol.

The other therapeutic agent can be an anti-addictive-disorder agent. Useful anti-addictive-disorder agents include, but are not limited to, tricyclic antidepressants; MAO inhibitors; glutamate antagonists, such as ketamine HCl, dextromethorphan, dextrorphan tartrate and dizocilpine (MK801); degrading enzymes, such as anesthetics and aspartate antagonists; GABA agonists, such as baclofen and muscimol HBr; reuptake blockers; degrading enzyme blockers; glutamate agonists, such as D-cycloserine, carboxyphenylglycine, L-glutamic acid, and cis-piperidine-2,3-dicarboxylic acid; aspartate agonists; GABA antagonists such as gabazine (SR-95531), saclofen, bicuculline, picrotoxin, and (+) apomorphine HCl; and dopamine antagonists, such as spiperone HCl, haloperidol, and (−) sulpiride.

The other therapeutic agent can be an anti-alcohol agent. Useful anti-alcohol agents include, but are not limited to, disulfiram and naltrexone.

The other therapeutic agent can be an anti-nicotine agent. Useful anti-nicotine agents include, but are not limited to, clonidine.

The other therapeutic agent can be an anti-opiate agent. Useful anti-opiate agents include, but are not limited to, methadone, clonidine, lofexidine, levomethadyl acetate HCl, naltrexone, and buprenorphine.

The other therapeutic agent can be an anti-cocaine agent. Useful anti-cocaine agents include, but are not limited to, desipramine, amantadine, fluoxidine, and buprenorphine.

The other therapeutic agent can be an appetite suppressant. Useful appetite suppressants include, but are not limited to, fenfluramine, phenylpropanolamine, and mazindol.

The other therapeutic agent can be an anti-lysergic acid diethylamide ("anti-LSD") agent. Useful anti-LSD agents include, but are not limited to, diazepam.

The other therapeutic agent can be an anti-phencyclidine ("anti-PCP") agent. Useful anti-PCP agents include, but are not limited to, haloperidol.

The other therapeutic agent can be an anti-Parkinson's-disease agent. Useful anti-Parkinson's-disease agents include, but are not limited to, dopamine precursors, such as levodopa, L-phenylalanine, and L-tyrosine; neuroprotective agents; dopamine agonists; dopamine reuptake inhibitors; anticholinergics such as amantadine and memantine; and 1,3,5-trisubstituted adamantanes, such as 1-amino-3,5-dimethyl-adamantane (U.S. Pat. No. 4,122,193 to Sherm et al.).

The other therapeutic agent can be an anti-depression agent. Useful anti-depression agents include, but are not limited to, amitriptyline, clomipramine, doxepine, imipramine, trimipramine, amoxapine, desipramine, maprotiline, nortriptyline, protripyline, fluoxetine, fluvoxamine, paroxetine, setraline, venlafaxine, bupropion, nefazodone, trazodone, phenelzine, tranylcypromine and selegiline.

The other therapeutic agent can be an anxiolytic agent. Useful anxiolytic agents include, but are not limited to, benzodiazepines, such as alprazolam, chlordiazepoxide, clonazepam, clorazepate, diazepam, halazepam, lorazepam, oxazepam, and prazepam; non-benzodiazepine agents, such as buspirone; and tranquilizers, such as barbituates.

The other therapeutic agent can be an antipsychotic drug. Useful antipsychotic drugs include, but are not limited to, phenothiazines, such as chlorpromazine, mesoridazine besylate, thioridazine, acetophenazine maleate, fluphenazine, perphenazine, and trifluoperazine; thioxanthenes, such as chlorprothixene, and thiothixene; and other hetercyclic compounds, such as clozapine, haloperidol, loxapine, molindone, pimozide, and risperidone. Preferable anti-psychotic drugs include chlorpromazine HCl, thioridazine HCl, fluphenazine HCl, thiothixene HCl, and molindone HCl.

The other therapeutic agent can be an anti-obesity drug. Useful anti-obesity drugs include, but are not limited, to β-adrenergic receptor agonists, preferably β-3 receptor agonists such as, but not limited to, fenfluramine; dexfenfluramine; sibutramine; bupropion; fluoxetine; phentermine; amphetamine; methamphetamine; dextroamphetamine; benzphetamine; phendimetrazine; diethylpropion; mazindol; phenylpropanolamine; norepinephrine-serotonin reuptake inhibitors, such as sibutramine; and pancreatic lipase inhibitors, such as orlistat.

5. EXAMPLE

(−)-1-(3,4-DICHLOROPHENYL)-3-AZABICYCLO[3.1.0]HEXANE Hydrochloride

To 279 mg of (±)-1-(3,4-dichlorophenyl)-3-azabicyclo[3.1.0]hexane hydrochloride obtained using the methods described in Epstein et al., *J. Med. Chem.*, 24:481–490 (1981) was added 7 mL of 9:1 hexane:isopropyl alcohol, followed by 8 drops of diethylamine. To the resulting mixture was added isopropyl alcohol, dropwise, until a solution was obtained. The solution was concentrated to a volume of 6 mL using a stream of helium gas, and six 1-mL portions of the concentrate were subjected to high-performance liquid chromatography using an HPLC instrument equipped with a 1 cm×25 cm Daicel CHIRALPAK AD column (Chiral Technologies, Inc., Exton, Pa.). Elution was carried out at ambient temperature using 95:5 (v/v) hexane:isopropyl alcohol solution containing 0.05% diethylamine as a mobile phase at a flow rate of 6 mL/min. The fraction eluting at about 26.08 to 34 minutes was collected and concentrated to provide a first residue, which was dissolved in a minimal amount of ethyl acetate. Using a stream of nitrogen, the ethyl acetate solution was evaporated to provide a second residue, which was dissolved in 1 mL of diethyl ether. To the diethyl ether solution was added 1 mL diethyl ether saturated with gaseous hydrochloric acid. A precipitate formed, which was filtered, washed with 2 mL of diethyl ether and dried to provide 33 mg of (−)-1-(3,4-dichlorophenyl)-3-azabicyclo[3.1.0]hexane hydrochloride of 88% enantiomeric excess. This material was repurified using the chromatography conditions described above. The fraction eluting at about 28 to about 34 minutes was concentrated, acidified, and dried, as described above, to provide 16.0 mg of (−)-1-(3,4-dichlorophenyl)-3-azabicyclo[3.1.0]hexane hydrochloride: optical rotation $[\alpha]^{25}_D = -56°$ in methanol at 2 mg/mL; 99.1% enantiomeric excess.

6. EXAMPLE

Activity Comparison of (−)-1-(3,4-DICHLOROPHENYL)-3-AZABICYCLO[3.1.0]HEXANE HCL and (+)-1-(3,4-DICHLOROPHENYL)-3-AZABICYCLO[3.1.0]HEXANE HCL in a Dopamine, Norepinephrine, and Serotonin Transporter Binding Assay Dopamine, norepinephrine, and serotonin uptake-inhibition activity of (−)-1-(3,4-dichlorophenyl)-3-azabicyclo[3.1.0]hexane hydrochloride was compared to that of (±)-1-(3,4-dichlorophenyl)-3-azabicyclo[3.1.0]hexane hydrochloride using a standard dopamine transporter binding assay.

6.1 Materials and Methods 6.1.1 Dopamine Transporter Assay

The dopamine uptake transporter binding assay was performed according to the methods described in Madras et al., 1989, *Mol. Pharmacol.* 36(4):518–524 and Javitch et al., 1984, *Mol. Pharmacol.* 26(1):35–44. The receptor source was guinea pig striatal membranes; the radioligand was [$^3$H]WIN 35,428 (DuPont-NEN, Boston, Mass.) (60–87 Ci/mmol) at a final ligand concentration of 2.0 nM; the non-specific determinant 1 μM 1-[2-[bis(4-Fluorophenyl)methoxy]ethyl]-4-[3-phenylpropyl]piperazine dihydrochloride ("GBR 12909"), a high-affinity dopamine uptake inhibitor; reference compound was also GBR 12909. (−)-1-(3,4-Dichlorophenyl)-3-azabicyclo[3.1.0]hexane HCl was obtained according to the method of Example 5, above. Reactions were carried out in 50 mM TRIS-HCl (pH 7.4), containing 120 mM NaCl and at 0° C. to 4° C. for two hours. The reaction was terminated by rapid vacuum filtration onto glass fiber filters. Radioactivity trapped in the filters was determined and compared to control values in order to ascertain the interactions of the test compound with the dopamine uptake site. The data are reported in Table 1 below.

6.1.2 Norepinephrine Transporter Assay

The norepinephrine transporter binding assay was performed according to the methods described in Raisman et al., 1982, *Eur. Jrnl. Pharmacol.* 78:345–351 and Langer et al., 1981, *Eur. Jrnl. Pharmacol.* 72:423. The receptor source was rat forebrain membranes; the radioligand was [$^3$H]nisoxetine (60–85 Ci/mmol) at a final ligand concentration of 1.0 nM; the non-specific determinant 1 μM desipramine ("DMI"), a high-affinity norepinephrine uptake inhibitor; reference compound was desipramine ("DMI"), imipramine, amitriptyline, or nisoxetine. (−)-1-(3,4-Dichlorophenyl)-3-azabicyclo[3.1.0]hexane HCl was obtained according to the method of Example 5, above. Reactions were carried out in 50 mM TRIS-HCl (pH 7.4), containing 300 mM NaCl and 5 mM KCl and at 0° C. to 4° C. for four hours. The reaction was terminated by rapid vacuum filtration onto glass fiber filters. Radioactivity trapped in the filters was determined and compared to control values in order to ascertain the interactions of the test compound with the norepinephrine uptake site. The data are reported in Table 2 below.

6.1.3 Serotonin Transporter Assay

The serotonin transporter binding assay was performed according to the methods described in D'Amato et al., 1987, *Jrnl. Pharmacol. & Exp. Ther.* 242:364–371 and Brown et al., 1986, *Eur. Jrnl. Pharmacol.* 123:161–165. The receptor source was human platelet membranes; the radioligand was [$^3$H]citalopram (70–87 Ci/mmol) at a final ligand concentration of 0.7 nM; the non-specific determinant 1 μM clomipramine, a high-affinity serotonin uptake inhibitor; reference compound was imipramine. (−)-1-(3,4-Dichlorophenyl)-3-azabicyclo[3.1.0]hexane HCl was obtained according to the method of Example 5, above. Reactions were carried out in 50 mM TRIS-HCl (pH 7.4), containing 120 mM NaCl and 5 mM KCl and at 25° C. for one hour. The reaction was terminated by rapid vacuum filtration onto glass fiber filters. Radioactivity trapped in the filters was determined and compared to control values in order to ascertain the interactions of the test compound with the serotonin uptake site. The data are reported in Table 3 below.

6.2 Results

TABLE 1

Dopamine Transporter Binding Assay

| Compound | Ki |
|---|---|
| (−)-1-(3,4-dichlorophenyl)-3-azabicyclo[3.1.0]hexane HCl | $2.61 \times 10^{-7}$ |
| (±)-1-(3,4-dichlorophenyl)-3-azabicyclo[3.1.0]hexane HCl | $1.54 \times 10^{-7}$ |
| GBR 12909 | $1.16 \times 10^{-8}$ |

TABLE 2

Norepinephrine Transporter Binding Assay

| Compound | Ki |
|---|---|
| (−)-1-(3,4-dichlorophenyl)-3-azabicyclo[3.1.0]hexane HCl | N/A |
| (±)-1-(3,4-dichlorophenyl)-3-azabicyclo[3.1.0]hexane HCl | $1.42 \times 10^{-7}$ |
| Desimipramine HCl ("DMI") | $1.13 \times 10^{-9}$ |

N/A = no measurable affinity

TABLE 3

Serotonin Transporter Binding Assay

| Compound | Ki |
|---|---|
| (−)-1-(3,4-dichlorophenyl)-3-azabicyclo[3.1.0]hexane HCl | N/A |
| (±)-1-(3,4-dichlorophenyl)-3-azabicyclo[3.1.0]hexane HCl | $1.87 \times 10^{-7}$ |
| Imipramine HCl | $2.64 \times 10^{-8}$ |

N/A = no measurable affinity

The data in Table 1 show that both (−)-1-(3,4-dichlorophenyl)-3-azabicyclo[3.1.0]hexane HCl and (+)-1-(3,4-dichlorophenyl)-3-azabicyclo[3.1.0]hexane HCl have affinity for the dopamine uptake site. Conversely, the data in Tables 2 and 3 show that the (+)-1-(3,4-dichlorophenyl)-3-azabicyclo[3.1.0]hexane HCl has affinity for the norepinephrine and serotonin uptake sites, wherein the (−)-1-(3,4-dichlorophenyl)-3-azabicyclo[3.1.0]hexane HCl has no measurable affinity for the norepinephrine and serotonin uptake sites. Although the (+)-1-(3,4-dichlorophenyl)-3-azabicyclo[3.1.0]hexane HCl has a higher binding affinity for the dopamine reuptake site than the (−)-1-(3,4-dichlorophenyl)-3-azabicyclo[3.1.0]hexane HCl, the use of the (−)-1-(3,4-dichlorophenyl)-3-azabicyclo[3.1.0]hexane HCl can be more advantageous than the (+)-1-(3,4-dichlorophenyl)-3-azabicyclo[3.1.0]hexane HCl for inhibiting dopamine uptake because of its specificity for inhibiting dopamine uptake. In other words, the use of the (−)-1-(3,4-dichlorophenyl)-3-azabicyclo[3.1.0]hexane HCl can prevent undesirable side effects associated with inhibiting norepinephrine uptake and serotonin uptake, such as hypertension and sexual dysfunction, respectively.

Successful inhibition of dopamine reuptake has been has been associated with the treatment of attention deficit disorder, depression, obesity, Parkinson's disease, a tic disorder and an addictive disorder (Hitri et al., 1994, *Clin. Pharmacol.* 17:1–22; Noble, 1994, *Alcohol Supp.* 2:35–43; and Blum et al., 1995, *Pharmacogenetics* 5:121–141). Because of its specificity for inhibiting dopamine uptake, (−)-1-(3,4-dichlorophenyl)-3-azabicyclo[3.1.0]hexane or a pharmaceutically acceptable salt thereof that is more advantageous than (+)-1-(3,4-dichlorophenyl)-3-azabicyclo[3.1.0]hexane or a pharmaceutically acceptable salt thereof for treating or preventing a disorder alleviated by inhibiting dopamine reuptake in a patient.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A method for treating a disorder alleviated by inhibiting dopamine reuptake, wherein the disorder is selected from the group consisting of attention deficit disorder, depression, obesity, Parkinson's disease, and a tic disorder, comprising administering to a patient in need of such treatment or prevention an effective amount of (−)-1-(3,4-dichlorophenyl)-3-azabicyclo[3.1.0]hexane or a pharmaceutically acceptable salt thereof, each being substantially free of its corresponding (+)-enantiomer.

2. The method according to claim 1, wherein the attention-deficit disorder is selected from the group consisting of attention-deficit/hyperactivity disorder, predominately inattentive type; attention-deficit/hyperactivity disorder, predominately hyperactivity-impulsive type; attention-deficit/hyperactivity disorder, combined type; conduct disorder; and oppositional defiant disorder.

3. The method according to claim 1, wherein the depression is selected from the group consisting of major depressive disorder, recurrent; dysthymic disorder; and major depressive disorder, single episode.

4. The method according to claim 1, wherein the Parkinson's disease is neuroleptic-induced parkinsonism.

5. The method according to claim 1, wherein the tic disorder is selected from the group consisting of Tourette's disorder, chronic motor disorder, vocal tic disorder, transient tic disorder, stuttering, autistic disorder, and somatization disorder.

6. A method for treating attention-deficit disorder alleviated by inhibiting dopamine reuptake, comprising administering to a patient in need of such treatment or prevention an effective amount of (−)-1-(3,4-dichlorophenyl)-3-azabicyclo[3.1.0]hexane or a pharmaceutically acceptable salt thereof, each being substantially free of its corresponding (+)-enantiomer.

7. The method according to claim 6, wherein the (−)-1-(3,4-dichlorophenyl)-3-azabicyclo[3.1.0]hexane or pharmaceutically acceptable salt thereof has no more than about 2% w/w of the corresponding (+)-enantiomer.

8. The method according to claim 6, wherein the (−)-1-(3,4-dichlorophenyl)-3-azabicyclo[3.1.0]hexane or pharmaceutically acceptable salt thereof has no more than about 1% w/w of the corresponding (+)-enantiomer.

9. The method according to claim 6, wherein the attention-deficit disorder is selected from the group consisting of attention-deficit/hyperactivity disorder, predominately inattentive type; attention-deficit/hyperactivity disorder, predominately hyperactivity-impulsive type; attention-deficit/hyperactivity disorder, combined type; conduct disorder; and oppositional defiant disorder.

10. A method for treating depression alleviated by inhabiting dopamine reutake, comprising administering to a patient in need of such treatment or prevention an effective amount of (−)-1-(3,4-dichlorophenyl)-3-azabicyclo[3.1.0]hexane or a pharmaceutically acceptable salt thereof, each being substantially free of its corresponding (+)-enantiomer.

11. The method according to claim 10, wherein the (−)-1-(3,4-dichlorophenyl)-3-azabicyclo[3.1.0]hexane or pharmaceutically acceptable salt thereof has no more than about 2% w/w of the corresponding (+)-enantiomer.

12. The method according to claim 10, wherein the (−)-1-(3,4-dichlorophenyl)-3-azabicyclo[3.1.0]hexane or pharmaceutically acceptable salt thereof has no more than about 1% w/w of the corresponding (+)-enantiomer.

13. The method according to claim 10, wherein the depression is selected from the group consisting of major depressive disorder, recurrent; dysthymic disorder; and major depressive disorder, single episode.

14. A method for treating obesity, alleviated by inhibiting dopamine reutake, comprising administering to a patient in need of such treatment or prevention an effective amount of (−)-1-(3,4-dichlorophenyl)-3-azabicyclo[3.1.0]hexane or a pharmaceutically acceptable salt thereof, each being substantially free of its corresponding (+)-enantiomer.

15. The method according to claim 14, wherein the (−)-1-(3,4-dichlorophenyl)-3-azabicyclo[3.1.0]hexane or pharmaceutically acceptable salt thereof has no more than about 2% w/w of the corresponding (+)-enantiomer.

16. The method according to claim 14, wherein the (−)-1-(3,4-dichlorophenyl)-3-azabicyclo[3.1.0]hexane or pharmaceutically acceptable salt thereof has no more than about 1% w/w of the corresponding (+)-enantiomer.

17. A method for treating Parkinson's disease alleviated by inhibiting dopamine reutake, comprising administering to a patient in need of such treatment or prevention an effective amount of (−)-1-(3,4-dichlorophenyl)-3-azabicyclo[3.1.0]hexane or a pharmaceutically acceptable salt thereof, each being substantially free of its corresponding (+)-enantiomer.

18. The method according to claim 17, wherein the (−)-1-(3,4-dichlorophenyl)-3-azabicyclo[3.1.0]hexane or pharmaceutically acceptable salt thereof has no more than about 2% w/w of the corresponding (+)-enantiomer.

19. The method according to claim 17, wherein the (−)-1-(3,4-dichlorophenyl)-3-azabicyclo[3.1.0]hexane or pharmaceutically acceptable salt thereof has no more than about 1% w/w of the corresponding (+)-enantiomer.

20. A method for treating a tic disorder, alleviated by inhibiting dopamine reutake, comprising administering to a patient in need of such treatment or prevention an effective amount of (−)-1-(3,4-dichlorophenyl)-3-azabicyclo[3.1.0]hexane or a pharmaceutically acceptable salt thereof, each being substantially free of its corresponding (+)-enantiomer.

21. The method according to claim 20, wherein the (−)-1-(3,4-dichlorophenyl)-3-azabicyclo[3.1.0]hexane or pharmaceutically acceptable salt thereof has no more than about 2% w/w of the corresponding (+)-enantiomer.

22. The method according to claim 20, wherein the (−)-1-(3,4-dichlorophenyl)-3-azabicyclo[3.1.0]hexane or pharmaceutically acceptable salt thereof has no more than about 1% w/w of the corresponding (+)-enantiomer.

23. The method according to claim 20, wherein the tic disorder is selected from the group consisting of Tourette's disorder, chronic motor disorder, vocal tic disorder, transient tic disorder, stuttering, autistic disorder, and somatization disorder.

* * * * *